United States Patent
Murphy

(10) Patent No.: US 9,295,755 B2
(45) Date of Patent: *Mar. 29, 2016

(54) MULTILAYER TISSUE REGENERATION SYSTEM

(75) Inventor: William L. Murphy, Madison, WI (US)

(73) Assignee: Wisconsin Alumni Research Foundation, Madison, WI (US)

(*) Notice: Subject to any disclaimer, the term of this patent is extended or adjusted under 35 U.S.C. 154(b) by 1129 days.

This patent is subject to a terminal disclaimer.

(21) Appl. No.: 11/583,231

(22) Filed: Oct. 18, 2006

(65) Prior Publication Data

US 2008/0095817 A1 Apr. 24, 2008

(51) Int. Cl.
A61K 38/18 (2006.01)
A61L 27/30 (2006.01)
A61L 27/32 (2006.01)
A61K 45/06 (2006.01)

(52) U.S. Cl.
CPC ............ *A61L 27/32* (2013.01); *A61K 38/1825* (2013.01); *A61K 38/1866* (2013.01); *A61K 38/1875* (2013.01); *A61K 45/06* (2013.01); *A61L 27/30* (2013.01); *A61L 27/306* (2013.01)

(58) Field of Classification Search
None
See application file for complete search history.

(56) References Cited

U.S. PATENT DOCUMENTS

| 6,767,928 | B1 | 7/2004 | Murphy et al. | |
|---|---|---|---|---|
| 2004/0126405 | A1* | 7/2004 | Sahatjian et al. | 424/423 |
| 2005/0069572 | A1* | 3/2005 | Williams et al. | 424/426 |

OTHER PUBLICATIONS

Rifkin et al., J. Cell Biol., 2010, vol. 190(6):949-951.*
Gilbert M, et al., "Chimeric peptides of statherin and ostepontin that bind hydroxyapatite and mediate cell adhesion," J. Biol. Chem. 275:16213-16218 (2000).
Harris N, et al., "Functional analysis of bone sialoprotein: identification of the hydroxyapatite-nucleating and cell-binding domains by recombinant pepetide expression and site-directed mutagenesis," Bone 27:795-802 (2000).
Murphy W, et al., "Sustained release of vascular endothelial grwoth factor from mineralized poly(lactide-co-glycide) scaffolds for tissue engineering," Biomaterials 21:2521-2527 (2000).
Stayton P, et al., "Molecular recognition at the protein-hydroxyapatite interface," Crit. Rev. Oral Biol. Med. 14:370-376 (2003).

* cited by examiner

*Primary Examiner* — Xiaozhen Xie
(74) *Attorney, Agent, or Firm* — Stinson Leonard Street LLC

(57) ABSTRACT

A system for growing tissue based upon layers of an inorganic matrix, wherein each layer of the inorganic matrix is designed to dissolve at a separate rate and result in sequential growth factor delivery upon its dissolution.

22 Claims, No Drawings

MULTILAYER TISSUE REGENERATION SYSTEM

STATEMENT REGARDING FEDERALLY SPONSORED RESEARCH OR DEVELOPMENT

This invention was made with United States government support awarded by the following agency: NIH R03-AR052893. The United States has certain rights in this invention.

CROSS-REFERENCE TO RELATED APPLICATIONS

Not applicable.

BACKGROUND

The invention relates generally to a tissue regeneration system, and more particularly to a system that includes a layered plurality of mineral matrices, where at least two of the layers include a biomolecule having a cell-affecting portion and a matrix-binding portion, and where the biomolecule is releasably associated with the matrix. In use, the plurality of mineral matrices degrade at various predictable rates, facilitating temporal control over release of the biomolecule(s) from the matrices.

One area of tissue regeneration that would benefit from improved biological surrogates is bone tissue regeneration systems. Under physiological conditions, bone tissue regeneration involves a complex interplay of multiple biologically active molecules and stem cells. The biologically active molecules are often presented sequentially in "cascades," where each factor has a distinct effect on the cells of a growing bone issue. These biologically active molecules can be exploited to direct active regeneration of functional bone tissue for repair or for replacement. A key issue in designing systems to aid in bone tissue regeneration is to temporally control tissue concentration of biologically active molecules such as growth factors and/or cytokines.

Regenerating natural bone tissue represents a promising approach to bone replacement and could supplant many of the current, metallic, hardware-based bone replacement methods and expand the range of orthopedic conditions that can be effectively treated. Potential applications of novel bone regeneration systems include filling of bone voids in nonunion fractures or maxillofacial deformities, bridging of gaps in spine fusion surgeries and stabilizing vertebral compression fractures. Not only would improved bone tissue regeneration systems offer an expanded range of treatment for orthopedic conditions, they would also be economically advantageous.

Existing passive bone tissue repairing or replacing systems do not exert a high level of control over the process of new bone formation. Such passive tissue regeneration systems include simply adding growth factors to a defect site in solution. However, such systems are inefficient because single growth factors delivered either by bolus injections into the site of disease or by systemic administration require very high levels for a measurable in vivo effect. In many instances, the growth factors will simply diffuse away from a defect site, leading to limited effects. Additionally, uncontrolled growth factor activity may occur at a distant site. See Yancopoulos G, et al., "Vascular-specific growth factors and blood vessel formation," Nature 407:242-248 (2000).

To solve these problems, recent tissue regeneration systems embed growth factors into plastic microspheres, thereby localizing growth factors to a defect site. See Langer R & Moses M, "Biocompatible controlled release polymers for delivery of polypeptides and growth factors," J. Cell Biochem. 45:340-345 (1991); Langer R, "New methods of drug delivery," Science 249:1527-1533 (1990); Leong K, et al., "Polyanhydrides for controlled release of bioactive agents," Biomaterials 7:364-371 (1986); Cohen S, et al., "Controlled delivery systems for proteins based on poly(lactic/glycolic acid) microspheres," Pharm. Res. 8:713-720 (1991); and Pekarek K, et al., "Double-walled polymer microspheres for controlled drug release," Nature 367:258-260 (1994). None of these systems, however, provides a structural matrix for tissue ingrowth. In addition, these systems are difficult to process into structural matrices while retaining adequate biological activity of the growth factor. Furthermore, many of these systems have failed to demonstrate the ability to temporally deliver multiple growth factors.

Other tissue regeneration systems embed growth factors in hydrated gels, thereby localizing growth factors to a defect site. See Lee K, et al., "Controlled growth factor release from synthetic extracellular matrices," Nature 408:998-1000 (2000); Tabata Y & Ikada Y, "Vascularization effect of basic fibroblast growth factor released from gelatin hydrogels with different biodegradabilities," Biomaterials 20:2169-2175 (1999); and Anseth K, et al., "In situ forming degradable networks and their application in tissue engineering and drug delivery," J. Control. Release 78:199-209 (2002). However, like plastic microspheres, hydrated gels are not particularly well-suited for certain types of tissue regeneration because the growth factors rapidly diffuse out of the gel matrix, resulting in limited signaling.

To overcome these problems, the most recent tissue regeneration systems have relied upon methods of gas foaming a porous plastic scaffold to allow for incorporation of growth factors with biological activity and variable release rates of several days to months. See Murphy W, et al., "Sustained release of vascular endothelial growth factor from mineralized poly(lactide-co-glycide) scaffolds for tissue engineering," Biomaterials 21:2521-2527 (2000); Murphy W, et al., "Bone regeneration via a mineral substrate and induced angiogenesis," J. Dent. Res. 83:204-210 (2004); Sheridan M, et al., "Bioabsorbable polymer scaffolds for tissue engineering capable of sustained growth factor delivery," J. Control. Release 64:94-102 (2000); Howdle S, et al., "Supercritical fluid mixing: preparation of thermally sensitive polymer composites containing bioactive materials," Chemical Commun. 1:1-2 (2001); and Yang X, et al., "Novel osteoinductive biomimetic scaffolds stimulate human osteoprogenitor activity—implications for skeletal repair," Connect. Tissue Res. 44:312-317 (2003). See also U.S. Pat. No. 6,676,928.

Similarly, others have used covalent conjugation of growth factors to hydrogels and multilayered hydrogels to provide enhanced control over osteogenic growth factor delivery. See Zisch A, et al., "Covalently conjugated VEGF-fibrin matrices for endothelialization," J. Control. Release 72:101-113 (2001); Raiche A & Puleo D, "Cell responses to BMP-2 and IGF-I released with different time-dependent profiles," J. Biomed. Mater. Res. 69A:342-350 (2004); and Raiche A & Puleo D, "In vitro effects of combined and sequential delivery of two bone growth factors," Biomaterials 25:677-685 (2004). These tissue regeneration systems, however, have not yet achieved satisfactory temporal control over cell activity while new tissue forms. In addition, these tissue regeneration systems have difficultly in temporally controlling the processing of heterogeneous and degradable materials with layers containing growth factors. Furthermore, none of these systems permits an adequate release of growth factors from a single matrix using release mechanisms that occur over distinct timeframes.

For the foregoing reasons, there is a need for a tissue regeneration system that localizes and temporally controls the release of multiple growth factors to stimulate tissue regeneration.

BRIEF SUMMARY

The present invention is summarized in that a system for regenerating tissue, including but not limited to bone, includes a template having layered therewith at least one synthetic, degradable extracellular matrix layer, where at least one layer has associated therewith (i.e. therein, thereon or both), at least one biomolecule having a cell-affecting portion and a matrix-binding portion, where the biomolecule is releasably associated with the matrix via the matrix-binding portion. In use, extracellular matrix layers dissolve and degrade under physiological conditions at predictable rates to facilitate release of the biomolecule from a matrix layer. The released biomolecule is bioactive and is in sufficiently close proximity to one or more cell types of interest to advantageously affect a cell-mediated bioactivity. When the system includes two or more matrix layers having distinct structural attributes, the layers can degrade at distinct rates. When distinct layers include distinct biomolecules, each biomolecule release can be temporally controlled.

In some embodiments, the extracellular matrix layer includes a biomolecule that does not natively interact with the matrix. In other embodiments, the extracellular matrix layer includes a biomolecule that natively interacts with the matrix.

In some embodiments, the matrix attracts the cells to the tissue regeneration system, in vivo or in vitro. In some embodiments, in vivo or in vitro, the cells associate with an outer surface of the layer-coated template. When the template is porous, the cells can associate with the pores of the template.

In some embodiments, the matrix-binding portion is a calcium-binding protein or a calcium-binding portion of the calcium-binding protein. In other embodiments, the matrix-binding portion is SEQ ID NO: 1. In still other embodiments, the matrix-binding portion is either SEQ ID NO: 2 or SEQ ID NO: 3.

In another aspect, the invention is summarized in that a method for making a matrix layer includes the step of combining, in a solution at a physiological temperature and a physiological pH, at least one species of biomolecule having a cell-affecting portion and a matrix-binding portion, and inorganic mineral ions, in the presence of a template having polar oxygen groups until a first inorganic mineral matrix layer containing matrix-associated biomolecules is deposited on the template surface.

In yet another aspect, the invention is summarized in that a method for making an inorganic matrix layer includes the steps of exposing inorganic mineral ions in a solution at a physiological temperature and a physiological pH to a template having polar oxygen groups on a surface thereof until an inorganic mineral matrix layer is deposited on the surface, and exposing at least one species of biomolecule having a cell-affecting portion and a matrix-binding portion to the layer until the layer has associated therewith the at least one species of biomolecule.

In certain embodiments, the polar oxygen groups can be carboxylic acids, phosphates, aldehydes, ketones, alcohols, carbonyls, hydroxyls or metal oxides.

In certain embodiments, the template can be polycarboxylates, polyanhydrides, poly(α-hydroxy esters), poly(ethylene terephthalate), poly(carbonates), poly(amides), poly(lactones), poly(saccharides) or poly(acrylates).

In certain embodiments, either of the aforementioned method steps are repeated at least twice, or both method steps are performed serially in either order, to deposit on the template a plurality of layered mineral matrices containing, or having provided therewith, matrix-associated biomolecules. Additionally, the mineral ions and the biomolecule can be exposed to the template together, such that the biomolecule is integrated into the layer as it forms. Relatedly, a biomolecule can be provided on a surface of an inorganic mineral matrix layer and a further inorganic mineral matrix layer can be provided on the first matrix layer to embed the biomolecule into a specific portion of the layered structure. The skilled person will appreciate that one in possession of this disclosure can produce a wide variety of layered configurations engineered for use under a variety of conditions, as will become apparent from the disclosure infra. In producing separate layers in a multi-layer system, the conditions under which the components are combined, and/or amount of components can be varied to yield distinct matrix layers having structures and dissolution properties distinct from the other layers.

The described embodiments of the present invention have many advantages, including that the materials are biocompatible and that all steps can be carried out at physiological temperatures and at physiological pH to maintain activity of the biologically active molecule.

It is an object of the present invention to temporally control growth factor signaling and thereby direct activities of associated cells, such as stem cells.

BRIEF DESCRIPTION OF THE DRAWINGS

Not applicable.

DETAILED DESCRIPTION OF PREFERRED EMBODIMENTS

Suitable template materials are advantageously organic and advantageously contain side chains having carboxylic acid groups that induce mineral layer nucleation and growth or can undergo hydrolytic degradation to provide such side chain groups. Aspartic acid and/or glutamic acid residues on the templates, are particularly advantageous in that both residues include a carboxylic acid side chain. These include polycarboxylates, polyanhydrides, poly(α-hydroxy esters), poly(ethylene terephthalate), poly(carbonates), poly (amides), poly(lactones), poly(saccharides) and poly(acrylates). The template materials are advantageously macroporous and have a molecular weight sufficiently high to allow for formation of a template. The template materials need not be porous. For example, the template can be a non-porous surface such as a spherical surface formed of, e.g., α-hydroxy esters, on which mineral layer nucleation and growth can occur. Other template surfaces for mineral layer nucleation can include metallic surfaces, such as titanium or other like metals known to be suited for use in implants.

The extracellular matrix layer or layers can include a bone-mineral matrix. Inorganic minerals suitable for producing a bone-mineral matrix layer include bone mineral ions, such as, but not limited to calcium and phosphate and combinations of bone mineral ions, such as calcium-phosphates. The bone mineral matrix can include, e.g., hydroxyapatite (HAP), α-tricalcium phosphate (α-TCP), β-tricalcium phosphate (β-TCP), amorphous calcium phosphate, dicalcium phosphate, octacalcium phosphate or calcium carbonate. Where the matrix includes a plurality of layers, separate layers having distinct dissolution profiles can be constructed upon the template. To control dissolution order, and, ultimately, delivery of the biomolecule(s), distinct layers are deposited upon the template. Under physiological conditions, solubility of calcium phosphate species adhere to the following trend: amorphous calcium phosphate>dicalcium phosphate>octacalcium phosphate>β-TCP>HAP. A dicalcium phosphate mineral will typically have a dissolution rate that is more than fifty times higher than that of HAP. Therefore, creation of a matrix with distinct calcium phosphate layers allows for a broad range of dissolution patterns.

Each layer can contain therein or thereon an active biomolecule targeted to the matrix via a matrix-binding portion. Dissolving layers containing no biomolecule can be included among the matrix layers to provide a delay between release of biomolecules or for other reasons. Suitable active biomolecules have a cell-affecting portion and a matrix-binding portion covalently or non-covalently associated with the cell-affecting portion. The cell-affecting portion of the biomolecule can include, e.g., a growth factor, a hormone, a cytokine, a nucleic acid molecule or a biologically-active portion of any of the foregoing, such as a bioactive motif. Suitable growth factors can include growth factors affecting differentiation, proliferation, migration or other cell activities. For example, bone morphogenetic protein-2 (BMP-2; SEQ ID NO:4) and fibroblast growth factor-2 (FGF-2; SEQ ID NO:5) are suitable cell-affecting portions, as are portions or motifs thereof that retain the growth factor activity. Other examples include bone morphogenetic protein-7 (BMP-7; SEQ ID NO:6) and vascular endothelial growth factor (VEGF; SEQ ID NO:7).

In some embodiments, the matrix-binding portion of the active biomolecules are amino acid sequences rich in glutamic acid, aspartic acid or phosphoserine, which interact directly with calcium ions in mineralized extracellular matrices and which are recognized in the art as binding well to bone minerals. See Gilbert M, et al., "Chimeric peptides of statherin and ostepontin that bind hydroxyapatite and mediate cell adhesion," J. Biol. Chem. 275:16213-16218 (2000); and Stayton P, et al., "Molecular recognition at the protein-hydroxyapatite interface," Crit. Rev. Oral Biol. Med. 14:370-376 (2003), each incorporated by reference in its entirety as if set forth herein. Particular amino acid sequences include EPRREVCEL (SEQ ID NO: 1), a mineral-binding fragment of osteocalcin, or SEQ ID NO:1 altered by extension to a length of at least about thirteen amino acids, for example with a series of heterotypic or homotypic residues (such as alanine, cysteine, leucine, methionine, glutamate, glutamine, histidine or lysine) that urge the matrix-binding portion into a preferred helical configuration. Likewise, mineral binding fragments comprising at least about eight consecutive glutamic acid residues, e.g., EEEEEEEE (SEQ ID NO: 2) or at least about eight consecutive aspartic acid residues, e.g., DDDDDDDD (SEQ ID NO: 3) are contemplated. Harris H, et al., "Functional analysis of bone sialoprotein: identification of the hydroxyapatite-nucleating and cell-binding domains by recombinant peptide expression and site-directed mutagenesis," Bone 27:795-802 (2000); and Tye C, et al., "Delineation of the hydroxyapatite-nucleating domains of bone sialoprotein," J. Biol. Chem. 278:7949-7955 (2003). Other bone proteins, such as, but not limited to, matrix Gla protein (MGP), bone sialoprotein, phosphoryn and osteonectin may also contain suitable mineral-binding sequences.

In other embodiments, the biomolecule may intrinsically have both a mineral-binding portion and a cell-affecting portion.

In use, bone tissue is regenerated in a subject having at a bone site an injury, a disease or a birth defect by providing the tissue regeneration system in or by directing the system to the site of the injury, disease or birth defect, whereupon the inorganic mineral layers sequentially dissolve, each layer's dissolution being dictated by the composition of its matrix.

The mineral layers described herein are developed by incubating the constituents in a "simulated body fluid" (SBF) or a "modified simulated body fluid" (mSBF) for five days or more at a pH of about 6.8 to about 7.4 and at a temperature of about 37° C. The SBF or mSBF is refreshed daily. This procedure produces a calcium-deficient, carbonate-containing apatite material on alginate and on poly-(α-hydroxy esters). See U.S. Pat. No. 6,767,928, incorporated herein by reference as if set forth in its entirety, for composition of SBF. mSBF includes elevated calcium and phosphate, as detailed infra. In general, an increase in pH favors hydroxyapatite growth, while a decrease in pH favors octacalcium phosphate mineral growth.

For example, conditions favorable for hydroxyapatite formation include a pH between about 5.0 and about 8.0 and a calcium concentration multiplied by a phosphate concentration between about $10^{-5}$ and about $10^{-8}$ M. Likewise, conditions favorable for octacalcium phosphate formation include a pH between about 6.0 and about 8.0 and a calcium concentration multiplied by a phosphate concentration between about $10^{-5}$ and about $10^{-7.5}$ M. Furthermore, conditions favorable for dicalcium phosphate dehydrate formation include a pH between about 6.0 and about 8.0 and a calcium concentration multiplied by a phosphate concentration between about $10^{-4}$ and about $10^{-6}$ M.

Specifically, using poly-(α-hydroxy esters) or alginate hydrogels as a template, one would vary the pH of mSBF between about 5.0 and about 6.0 to promote hydroxyapatite formation. Similarly, one would vary the pH of mSBF between about 6.0 and about 6.5 to promote octacalcium phosphate and hydroxyapatite formation. Likewise, one would vary the pH of mSBF between about 6.5 and about 8.0 to promote dicalcium phosphate, octacalcium phosphate and hydryoxyapatite formation.

EXAMPLES

Example 1

Matrices with an Organic Template and Two Inorganic Mineral Layers Embedded with Distinct Biologically Active Molecules At least two calcium phosphate-based mineral layers, each having a distinct dissolution pattern and having a distinct growth factor, are engineered into/onto an organic template. Standard alginate processing methods are used to crosslink alginate with calcium, resulting in a solid hydrogel template having a high density of carboxylic acid groups is formed. The template is freeze-dried until the hydrogel undergoes a phase separation and develops large, interconnected macropores (50-200 µm). See Lin H, et al., "Porous alginate/HAP sponges for bone tissue engineering," Materials Science Forum 426-432:343-3048 (2003), incorporated herein by reference as if set for in its entirety.

After processing, a HAP layer having a cross-sectional height of about 10 µm to about 1000 µm, is deposited on the hydrogel template at a physiological temperature in the range of about 35° C. to about 39° C. and at a physiological pH between about 5 and about 10 for 1 to 30 days, while retaining the macroporous structure of the template. The hydrogel template is incubated in a first mSBF solution containing ionic constituents of blood plasma, to initiate growth of a HAP layer, plus elevated levels of calcium (about 2.5 mM to about 25 mM) and phosphate (about 1 mM to about 10 mM) relative to conventional SBF, as well as a BMP-2 peptide (SEQ ID NO: 4) engineered using conventional methods to include the bone-mineral-binding sequence (SEQ ID NO: 1) at its C-terminal end. See U.S. Pat. No. 5,767,928, incorporated herein by reference as if set forth in its entirety; see also Bunker B, et al., "Ceramic thin film formation on functionalized interfaces through biomimetic processing," Science 264:48-55 (1994); and Ngankam P, et al., "Influence of polyelectrolyte multilayer films on calcium phosphate nucleation," J. Am. Chem. Soc. 122:8998-9004 (2000). Additionally or optionally, the octacalcium layer could include a BMP-7 peptide (SEQ ID NO: 6) engineered using conventional methods to include the bone-mineral-binding sequence (SEQ ID NO: 1) at its C-terminal end.

After production of the HAP layer, an octacalcium phosphate layer having a cross-sectional height of about 10 μm to about 100 μm is deposited on the HAP layer at a physiological temperature in the range of about 35° C. to about 39° C. at a physiological pH between about 6 and about 8 for 1 to 30 days, while retaining the macroporous structure of the template. The template with HAP layer is incubated in a second mSBF solution containing ionic constituents of blood plasma to initiate growth of the octacalcium phosphate layer, plus elevated levels of calcium (about 2.5 mM to about 25 mM) and phosphate (about 1 mM to about 10 mM) relative to conventional SBF, as well as an FGF-2 peptide (SEQ ID NO: 5) engineered using conventional methods to include the bone-mineral-binding sequence (SEQ ID NO:1) at its C-terminal end. Additionally or optionally, the HAP layer could include a VEGF peptide (SEQ ID NO: 7) engineered using conventional methods to include the bone-mineral-binding sequence (SEQ ID NO: 1) at its C-terminal end.

Following the second incubation, the hydrogel template has coated thereupon the inner HAP layer containing the engineered BMP-2 peptide and the outer octacalcium phosphate layer containing the engineered FGF-2 peptide. Each layer can contain a plurality of bioactive molecules, or no bioactive molecule, as desired.

FGF-2 and BMP-2 each display optimal in vitro biological activity at approximately 1 nM. The low optimal concentrations coupled with the ability to deliver the growth factors in a sustained manner over time permits inclusion of miniscule amounts of growth factors into a growing mineral matrix. This small amount of total protein included into the matrix avoids significant interference with mineral growth, as interference with mineral growth by acidic proteins typically occurs at higher protein concentrations.

The dissolution patterns of the HAP and octacalcium phosphate layers establish the rate of growth factor release from the matrix, which is a key parameter in controlling cell activity within the matrix. To establish the dissolution pattern, one varies the layers of mineral growth within the hydrogel template by systematically varying calcium concentration and pH. One should expect that a calcium concentration near that of blood plasma (2.5 mM) would result in formation of an HAP. Therefore, variations in calcium concentrations lead to formation of distinct calcium phosphate mineral layers. Other factors including, but not limited to, ionic concentrations of the solution, pH, surface energy of the template material and temperature can affect the type of calcium phosphate mineral layers.

Example 2

Temporal Control Over Mesenchymal Stem Cell Activity Via Sequential Growth Factor Release A. This example describes an important new approach to control in vitro and in vivo bone regeneration, by specifically demonstrating that the matrices of the invention can control stem cell activity in regenerating bone tissue by delivering growth factors that drive proliferation (FGF-2) and then differentiation (BMP-2) of mesenchymal stem cells (MSC) into functional osteoblasts. BMP-2 and FGF-2 have been chosen for their ability to elicit specific MSC activities and their importance in bone development and repair.

B. MSC are seeded into the octacalcium phosphate/HAP layered matrices of Example 1. The matrices deliver FGF-2 over one week in culture. At twenty-four hour intervals after initial cell seeding, cells are removed from the scaffolds via trypsinization and counted. To demonstrate cell proliferation in response to FGF-2, total cell number in matrices releasing FGF-2 is compared to cell number in control matrices without growth factor.

MSC cultured in matrices releasing FGF-2 retain their ability to differentiate down multiple lineages. To confirm the specific effect of FGF-2 on MSC proliferation, cell populations removed from the FGF-2-releasing matrices via trypsinizaiton are cultured for seven days. The cells are replated in culture and are induced to differentiate into chondrocytes, adipocytes and osteoblasts. The methods to analyze differentiation of MSC into osteoblasts (alizarin red staining of mineral), adipocytes (oil red O staining of lipid vacuoles) and chondrocytes (staining of type II collagen matrix) are known to the skilled artisan and cocktails for induction of differentiation are commercially available (Cambrex, Inc. Baltimore, Md.).

C. Response of Mesenchymal Stem Cells to BMP-2 Delivery: MSC are seeded into octacalcium phosphate/HAP layered matrices wherein no FGF-2 is provided in the octacalcium phosphate layer. The matrices, therefore, release no growth factor for one week and then release BMP-2 from the HAP layer for four weeks. During the BMP-2 release period, matrices are analyzed for osteogenic activity at five day intervals. Matrices are demineralized, paraffin-embedded, sectioned, stained for bone matrix deposition and imaged using an Olympus IX-71 microscope with a Hamamatsu 285 digital camera. Immunostaining for bone sialoprotein, OCN and osteonectin identifies regions of bone matrix deposition. Sections are also stained with Goldner's Trichrome, which stains osteoid red and mature bone matrix bright green. Additionally, the density of positively stained tissue grown within the matrices is quantified using Simple PCI image analysis software (Hamamatsu, Inc. Tokyo, JP).]

D. Sequential Delivery of FGF-2 and BMP-2 to Mesenchymal Stem Cells: In Vitro: MSC are incubated in mesenchymal stem cell growth medium at 37° C., pH 7.4, with 5% $CO_2$ and 95% humidity with matrices designed to release FGF-2 (one to ten days) followed by BMP-2 (four weeks) and analyzed for deposition of bone matrix as described previously. Bone matrix deposition is observed. Increasing the timeframe of FGF-2 release increases the total number of MSC and results in a larger population of cells capable of responding to BMP-2 induction. Accordingly, total bone matrix deposition increases with increased FGF-2 delivery.

While the invention is susceptible to various modifications and alternative forms, specific embodiments thereof have been shown by way of example in the drawings and are herein described below in detail. It should be understood, however, that the description of specific embodiments is not intended to limit the invention to cover all modification, equivalents and alternatives falling within the spirit and scope of the invention as defined by the appended claims.

The invention claimed is:

1. A tissue regeneration system comprising:
   a template having thereupon at least one synthetic, degradable extracellular matrix layer; and
   at least one biomolecule releasably associated with the layer, the biomolecule comprising a cell-affecting portion and a matrix-binding portion, wherein the cell-affecting portion is selected from the group consisting of fibroblast growth factor 2, bone morphogenetic protein-2, bone morphogenetic protein-7 and vascular endothelial growth factor.

2. A tissue regeneration system as recited in claim 1, wherein the template comprises polar oxygen groups.

3. A tissue regeneration system as recited in claim 2, wherein the polar oxygen groups are selected from the group consisting of carboxylic acids, phosphates, aldehydes, ketones, alcohols, carbonyls, hydroxyls and metal oxides.

4. A tissue regeneration system as recited in claim 1, wherein the template is selected from the group consisting of polycarboxylates, polyanhydrides, poly(α-hydroxy esters), poly(ethylene terephthalate), poly(carbonates), poly(amides), poly(lactones), poly(saccharides) and poly(acrylates).

5. A tissue regeneration system as recited in claim 1, wherein the extracellular matrix layer comprises ions of a mineral.

6. A tissue regeneration system as recited in claim 5, wherein the mineral is selected from the group consisting of hydroxyapatite, α-tricalcium phosphate, β-tricalcium phosphate, amorphous calcium phosphate, dicalcium phosphate, octacalcium phosphate and calcium carbonate.

7. A tissue regeneration system as recited in claim 1, wherein the at least one biomolecule does not natively interact with the matrix.

8. A tissue regeneration system as recited in claim 1, wherein the matrix-binding portion is a calcium-binding protein or a calcium-binding portion of a calcium-binding protein.

9. A tissue regeneration system as recited in claim 1, wherein the matrix-binding portion is selected from the group consisting of SEQ ID NOs: 1-3.

10. A tissue regeneration system as recited in claim 1, further comprising cells associated with an outer surface of the template.

11. A tissue regeneration system as recited in claim 10, wherein the template defines pores therein and wherein the cells are associated with the pores.

12. A method for making a tissue regeneration system as recited in claim 1, comprising the step of:
exposing ions of an inorganic mineral in a solution at a physiological temperature and pH to a template until an inorganic mineral matrix layer is deposited on the surface of the template; and
exposing at least one biomolecule having a cell-affecting portion and a matrix-binding portion to the matrix layer until the matrix layer has associated therewith the at least one biomolecule, wherein the cell-affecting portion is selected from the group consisting of fibroblast growth factor 2, bone morphogenetic protein-2, bone morphogenetic protein-7 and vascular endothelial growth factor.

13. A method as recited in claim 12, wherein the template has polar oxygen groups on a surface thereof, and wherein the polar oxygen groups are selected from the group consisting of carboxylic acids, phosphates, aldehydes, ketones, alcohols, carbonyls, hydroxyls or metal oxides.

14. A method as recited in claim 12, wherein the template is selected from the group consisting of polycarboxylates, polyanhydrides, poly(α-hydroxy esters), poly(ethylene terephthalate), poly(carbonates), poly(amides), poly(lactones), poly(saccharides) and poly(acrylates).

15. A method as recited in claim 12, wherein the mineral is selected from the group consisting of hydroxyapatite, α-tricalcium phosphate, β-tricalcium phosphate, amorphous calcium phosphate, dicalcium phosphate, octacalcium phosphate and calcium carbonate.

16. A method as recited in claim 12, wherein the cell-affecting portion comprises SEQ ID NO: 4.

17. A method as recited in claim 12, wherein the cell-affecting portion comprises SEQ ID NO: 5.

18. A method as recited in claim 12, wherein the cell-affecting portion comprises SEQ ID NO: 6.

19. A method as recited in claim 12, wherein the cell-affecting portion comprises SEQ ID NO: 7.

20. A method as recited in claim 12, wherein the matrix-binding portion is selected from the group consisting of SEQ ID NOs: 1-3.

21. A method as recited in claim 12, wherein the exposing step is repeated at least twice to deposit on the template a plurality of layered mineral matrices having at least one biomolecule associated therewith.

22. A method as recited in claim 12, wherein the at least one biomolecule is provided on the surface of a first layer, and a second layer is provided on the surface of the first layer.

* * * * *

SEQUENCE LISTING

```
<160> NUMBER OF SEQ ID NOS: 7

<210> SEQ ID NO 1
<211> LENGTH: 9
<212> TYPE: PRT
<213> ORGANISM: Artificial
<220> FEATURE:
<223> OTHER INFORMATION: Synthetic peptide

<400> SEQUENCE: 1

Glu Pro Arg Arg Glu Val Cys Glu Leu
1               5

<210> SEQ ID NO 2
<211> LENGTH: 8
<212> TYPE: PRT
<213> ORGANISM: Artificial
<220> FEATURE:
<223> OTHER INFORMATION: Synthetic peptide

<400> SEQUENCE: 2

Glu Glu Glu Glu Glu Glu Glu Glu
1               5

<210> SEQ ID NO 3
<211> LENGTH: 8
<212> TYPE: PRT
<213> ORGANISM: Artificial
<220> FEATURE:
<223> OTHER INFORMATION: Synthetic peptide

<400> SEQUENCE: 3

Asp Asp Asp Asp Asp Asp Asp Asp
1               5

<210> SEQ ID NO 4
<211> LENGTH: 396
<212> TYPE: PRT
<213> ORGANISM: Homo sapiens

<400> SEQUENCE: 4

Met Val Ala Gly Thr Arg Cys Leu Leu Ala Leu Leu Leu Pro Gln Val
1               5                   10                  15

Leu Leu Gly Gly Ala Ala Gly Leu Val Pro Glu Leu Gly Arg Arg Lys
                20                  25                  30

Phe Ala Ala Ala Ser Ser Gly Arg Pro Ser Ser Gln Pro Ser Asp Glu
            35                  40                  45

Val Leu Ser Glu Phe Glu Leu Arg Leu Leu Ser Met Phe Gly Leu Lys
        50                  55                  60

Gln Arg Pro Thr Pro Ser Arg Asp Ala Val Val Pro Pro Tyr Met Leu
65                  70                  75                  80

Asp Leu Tyr Arg Arg His Ser Gly Gln Pro Gly Ser Pro Ala Pro Asp
                85                  90                  95

His Arg Leu Glu Arg Ala Ala Ser Arg Ala Asn Thr Val Arg Ser Phe
            100                 105                 110

His His Glu Glu Ser Leu Glu Glu Leu Pro Glu Thr Ser Gly Lys Thr
        115                 120                 125
```

-continued

```
Thr Arg Arg Phe Phe Phe Asn Leu Ser Ser Ile Pro Thr Glu Glu Phe
    130                 135                 140

Ile Thr Ser Ala Glu Leu Gln Val Phe Arg Glu Gln Met Gln Asp Ala
145                 150                 155                 160

Leu Gly Asn Asn Ser Ser Phe His His Arg Ile Asn Ile Tyr Glu Ile
                165                 170                 175

Ile Lys Pro Ala Thr Ala Asn Ser Lys Phe Pro Val Thr Arg Leu Leu
            180                 185                 190

Asp Thr Arg Leu Val Asn Gln Asn Ala Ser Arg Trp Glu Ser Phe Asp
        195                 200                 205

Val Thr Pro Ala Val Met Arg Trp Thr Ala Gln Gly His Ala Asn His
210                 215                 220

Gly Phe Val Val Glu Val Ala His Leu Glu Glu Lys Gln Gly Val Ser
225                 230                 235                 240

Lys Arg His Val Arg Ile Ser Arg Ser Leu His Gln Asp Glu His Ser
                245                 250                 255

Trp Ser Gln Ile Arg Pro Leu Leu Val Thr Phe Gly His Asp Gly Lys
            260                 265                 270

Gly His Pro Leu His Lys Arg Glu Lys Arg Gln Ala Lys His Lys Gln
        275                 280                 285

Arg Lys Arg Leu Lys Ser Ser Cys Lys Arg His Pro Leu Tyr Val Asp
    290                 295                 300

Phe Ser Asp Val Gly Trp Asn Asp Trp Ile Val Ala Pro Pro Gly Tyr
305                 310                 315                 320

His Ala Phe Tyr Cys His Gly Glu Cys Pro Phe Pro Leu Ala Asp His
                325                 330                 335

Leu Asn Ser Thr Asn His Ala Ile Val Gln Thr Leu Val Asn Ser Val
            340                 345                 350

Asn Ser Lys Ile Pro Lys Ala Cys Cys Val Pro Thr Glu Leu Ser Ala
        355                 360                 365

Ile Ser Met Leu Tyr Leu Asp Glu Asn Glu Lys Val Val Leu Lys Asn
    370                 375                 380

Tyr Gln Asp Met Val Val Glu Gly Cys Gly Cys Arg
385                 390                 395

<210> SEQ ID NO 5
<211> LENGTH: 288
<212> TYPE: PRT
<213> ORGANISM: Homo sapiens

<400> SEQUENCE: 5

Met Val Gly Val Gly Gly Asp Val Glu Asp Val Thr Pro Arg Pro
1               5                   10                  15

Gly Gly Cys Gln Ile Ser Gly Arg Ala Ala Arg Gly Cys Asn Gly Ile
                20                  25                  30

Pro Gly Ala Ala Ala Trp Glu Ala Ala Leu Pro Arg Arg Arg Pro Arg
            35                  40                  45

Arg His Pro Ser Val Asn Pro Arg Ser Arg Ala Ala Gly Ser Pro Arg
        50                  55                  60

Thr Arg Gly Arg Thr Glu Glu Arg Pro Ser Gly Ser Arg Leu Gly
65                  70                  75                  80

Asp Arg Gly Arg Gly Arg Ala Leu Pro Gly Gly Arg Leu Gly Arg
                85                  90                  95

Gly Arg Gly Arg Ala Pro Glu Arg Val Gly Gly Arg Gly Arg Gly Arg
            100                 105                 110
```

Gly Thr Ala Ala Pro Arg Ala Ala Pro Ala Ala Arg Gly Ser Arg Pro
            115                 120                 125

Gly Pro Ala Gly Thr Met Ala Ala Gly Ser Ile Thr Thr Leu Pro Ala
130                 135                 140

Leu Pro Glu Asp Gly Gly Ser Gly Ala Phe Pro Pro Gly His Phe Lys
145                 150                 155                 160

Asp Pro Lys Arg Leu Tyr Cys Lys Asn Gly Gly Phe Phe Leu Arg Ile
                165                 170                 175

His Pro Asp Gly Arg Val Asp Gly Val Arg Glu Lys Ser Asp Pro His
                180                 185                 190

Ile Lys Leu Gln Leu Gln Ala Glu Glu Arg Gly Val Val Ser Ile Lys
            195                 200                 205

Gly Val Cys Ala Asn Arg Tyr Leu Ala Met Lys Glu Asp Gly Arg Leu
        210                 215                 220

Leu Ala Ser Lys Cys Val Thr Asp Glu Cys Phe Phe Phe Glu Arg Leu
225                 230                 235                 240

Glu Ser Asn Asn Tyr Asn Thr Tyr Arg Ser Arg Lys Tyr Thr Ser Trp
                245                 250                 255

Tyr Val Ala Leu Lys Arg Thr Gly Gln Tyr Lys Leu Gly Ser Lys Thr
            260                 265                 270

Gly Pro Gly Gln Lys Ala Ile Leu Phe Leu Pro Met Ser Ala Lys Ser
        275                 280                 285

<210> SEQ ID NO 6
<211> LENGTH: 431
<212> TYPE: PRT
<213> ORGANISM: Homo sapiens

<400> SEQUENCE: 6

Met His Val Arg Ser Leu Arg Ala Ala Pro His Ser Phe Val Ala
1               5                   10                  15

Leu Trp Ala Pro Leu Phe Leu Leu Arg Ser Ala Leu Ala Asp Phe Ser
            20                  25                  30

Leu Asp Asn Glu Val His Ser Ser Phe Ile His Arg Arg Leu Arg Ser
        35                  40                  45

Gln Glu Arg Arg Glu Met Gln Arg Glu Ile Leu Ser Ile Leu Gly Leu
    50                  55                  60

Pro His Arg Pro Arg Pro His Leu Gln Gly Lys His Asn Ser Ala Pro
65                  70                  75                  80

Met Phe Met Leu Asp Leu Tyr Asn Ala Met Ala Val Glu Glu Gly Gly
                85                  90                  95

Gly Pro Gly Gly Gln Gly Phe Ser Tyr Pro Tyr Lys Ala Val Phe Ser
            100                 105                 110

Thr Gln Gly Pro Pro Leu Ala Ser Leu Gln Asp Ser His Phe Leu Thr
        115                 120                 125

Asp Ala Asp Met Val Met Ser Phe Val Asn Leu Val Glu His Asp Lys
    130                 135                 140

Glu Phe Phe His Pro Arg Tyr His His Arg Glu Phe Arg Phe Asp Leu
145                 150                 155                 160

Ser Lys Ile Pro Glu Gly Glu Ala Val Thr Ala Ala Glu Phe Arg Ile
                165                 170                 175

Tyr Lys Asp Tyr Ile Arg Glu Arg Phe Asp Asn Glu Thr Phe Arg Ile
            180                 185                 190

Ser Val Tyr Gln Val Leu Gln Glu His Leu Gly Arg Glu Ser Asp Leu

```
                    195                 200                 205
Phe Leu Leu Asp Ser Arg Thr Leu Trp Ala Ser Glu Glu Gly Trp Leu
210                 215                 220

Val Phe Asp Ile Thr Ala Thr Ser Asn His Trp Val Asn Pro Arg
225                 230                 235                 240

His Asn Leu Gly Leu Gln Leu Ser Val Glu Thr Leu Asp Gly Gln Ser
                    245                 250                 255

Ile Asn Pro Lys Leu Ala Gly Leu Ile Gly Arg His Gly Pro Gln Asn
                260                 265                 270

Lys Gln Pro Phe Met Val Ala Phe Lys Ala Thr Glu Val His Phe
                275                 280                 285

Arg Ser Ile Arg Ser Thr Gly Ser Lys Gln Arg Ser Gln Asn Arg Ser
290                 295                 300

Lys Thr Pro Lys Asn Gln Glu Ala Leu Arg Met Ala Asn Val Ala Glu
305                 310                 315                 320

Asn Ser Ser Ser Asp Gln Arg Gln Ala Cys Lys Lys His Glu Leu Tyr
                    325                 330                 335

Val Ser Phe Arg Asp Leu Gly Trp Gln Asp Trp Ile Ile Ala Pro Glu
                340                 345                 350

Gly Tyr Ala Ala Tyr Tyr Cys Glu Gly Glu Cys Ala Phe Pro Leu Asn
                355                 360                 365

Ser Tyr Met Asn Ala Thr Asn His Ala Ile Val Gln Thr Leu Val His
                370                 375                 380

Phe Ile Asn Pro Glu Thr Val Pro Lys Pro Cys Cys Ala Pro Thr Gln
385                 390                 395                 400

Leu Asn Ala Ile Ser Val Leu Tyr Phe Asp Asp Ser Ser Asn Val Ile
                    405                 410                 415

Leu Lys Lys Tyr Arg Asn Met Val Val Arg Ala Cys Gly Cys His
                420                 425                 430

<210> SEQ ID NO 7
<211> LENGTH: 412
<212> TYPE: PRT
<213> ORGANISM: Homo sapiens

<400> SEQUENCE: 7

Met Thr Asp Arg Gln Thr Asp Thr Ala Pro Ser Pro Ser Tyr His Leu
1               5                   10                  15

Leu Pro Gly Arg Arg Thr Val Asp Ala Ala Ser Arg Gly Gln
                20                  25                  30

Gly Pro Glu Pro Ala Pro Gly Gly Val Gly Val Gly Ala Arg
                35                  40                  45

Gly Val Ala Leu Lys Leu Phe Val Gln Leu Leu Gly Cys Ser Arg Phe
50                  55                  60

Gly Gly Ala Val Val Arg Ala Gly Glu Ala Glu Pro Ser Gly Ala Ala
65                  70                  75                  80

Arg Ser Ala Ser Ser Gly Arg Glu Glu Pro Gln Pro Glu Glu Gly Glu
                85                  90                  95

Glu Glu Glu Glu Lys Glu Glu Glu Arg Gly Pro Gln Trp Arg Leu Gly
                100                 105                 110

Ala Arg Lys Pro Gly Ser Trp Thr Gly Glu Ala Ala Val Cys Ala Asp
                115                 120                 125

Ser Ala Pro Ala Ala Arg Ala Pro Gln Ala Leu Ala Arg Ala Ser Gly
                130                 135                 140
```

```
Arg Gly Gly Arg Val Ala Arg Arg Gly Ala Glu Glu Ser Gly Pro Pro
145                 150                 155                 160

His Ser Pro Ser Arg Arg Gly Ser Ala Ser Arg Ala Gly Pro Gly Arg
                165                 170                 175

Ala Ser Glu Thr Met Asn Phe Leu Leu Ser Trp Val His Trp Ser Leu
                180                 185                 190

Ala Leu Leu Leu Tyr Leu His His Ala Lys Trp Ser Gln Ala Ala Pro
                195                 200                 205

Met Ala Glu Gly Gly Gly Gln Asn His His Glu Val Val Lys Phe Met
210                 215                 220

Asp Val Tyr Gln Arg Ser Tyr Cys His Pro Ile Glu Thr Leu Val Asp
225                 230                 235                 240

Ile Phe Gln Glu Tyr Pro Asp Glu Ile Glu Tyr Ile Phe Lys Pro Ser
                245                 250                 255

Cys Val Pro Leu Met Arg Cys Gly Gly Cys Cys Asn Asp Glu Gly Leu
                260                 265                 270

Glu Cys Val Pro Thr Glu Glu Ser Asn Ile Thr Met Gln Ile Met Arg
                275                 280                 285

Ile Lys Pro His Gln Gly Gln His Ile Gly Glu Met Ser Phe Leu Gln
290                 295                 300

His Asn Lys Cys Glu Cys Arg Pro Lys Lys Asp Arg Ala Arg Gln Glu
305                 310                 315                 320

Lys Lys Ser Val Arg Gly Lys Gly Lys Gly Gln Lys Arg Lys Arg Lys
                325                 330                 335

Lys Ser Arg Tyr Lys Ser Trp Ser Val Tyr Val Gly Ala Arg Cys Cys
                340                 345                 350

Leu Met Pro Trp Ser Leu Pro Gly Pro His Pro Cys Gly Pro Cys Ser
                355                 360                 365

Glu Arg Arg Lys His Leu Phe Val Gln Asp Pro Gln Thr Cys Lys Cys
                370                 375                 380

Ser Cys Lys Asn Thr Asp Ser Arg Cys Lys Ala Arg Gln Leu Glu Leu
385                 390                 395                 400

Asn Glu Arg Thr Cys Arg Cys Asp Lys Pro Arg Arg
                405                 410
```